United States Patent
Guenther

(10) Patent No.: US 11,295,441 B2
(45) Date of Patent: Apr. 5, 2022

(54) ULTRASOUND IMAGE GENERATING SYSTEM

(71) Applicant: Fraunhofer-Gesellschaft zur Foerderung der angewandten Forschung e.V., Munich (DE)

(72) Inventor: Matthias Guenther, Bremen (DE)

(73) Assignee: Fraunhofer-Gesellschaft zur Förderung der angewandten Forschung e.V., Munich (DE)

(*) Notice: Subject to any disclaimer, the term of this patent is extended or adjusted under 35 U.S.C. 154(b) by 0 days.

(21) Appl. No.: 16/762,862

(22) PCT Filed: Nov. 7, 2018

(86) PCT No.: PCT/EP2018/080495
§ 371 (c)(1),
(2) Date: May 8, 2020

(87) PCT Pub. No.: WO2019/092033
PCT Pub. Date: May 16, 2019

(65) Prior Publication Data
US 2020/0286228 A1 Sep. 10, 2020

(30) Foreign Application Priority Data
Nov. 8, 2017 (DE) ...................... 10 2017 126 158.3

(51) Int. Cl.
*G06K 9/00* (2006.01)
*G06T 7/00* (2017.01)
(Continued)

(52) U.S. Cl.
CPC ............. *G06T 7/0012* (2013.01); *G06N 3/04* (2013.01); *G06N 3/08* (2013.01); *G06T 7/70* (2017.01);
(Continued)

(58) Field of Classification Search
CPC ................................ A61B 8/5207; A61B 8/14
See application file for complete search history.

(56) References Cited

U.S. PATENT DOCUMENTS

2005/0288584 A1* 12/2005 McMorrow ............ A61B 8/565
600/437
2014/0082542 A1* 3/2014 Zhang .................... G16H 30/40
715/771
(Continued)

FOREIGN PATENT DOCUMENTS

CN 106373109 2/2017
JP 2010264231 11/2010
(Continued)

OTHER PUBLICATIONS

Chartsias, Agisilaos, et al., "Adversarial Image Synthesis for Unpaired Multi-Modal Cardiac Data," University of Edinburgh, Edinburgh, UK, Cedars Sinai Medical Center, Los Angeles, US, 2017, 10 pages.
(Continued)

*Primary Examiner* — Hadi Akhavannik
(74) *Attorney, Agent, or Firm* — Lowe Graham Jones LLC; Ellen M. Bierman

(57) ABSTRACT

The invention relates to an ultrasound image generating system for generating an image of an object. The ultrasound image generating system comprises an ultrasound data provisioning unit for providing raw ultrasound data of the object, which data have been acquired using an ultrasound imaging modality. A trained unit provisioning unit provides a unit trained by machine learning, such as a trained neural network, which is configured to generate an ultrasound image of an object based on of raw ultrasound data of the object that does not correspond to the ultrasound imaging modality. An image generating unit generates the image of
(Continued)

the object using the provided trained unit, based on of the provided raw ultrasound data of the object.

18 Claims, 5 Drawing Sheets

(51) Int. Cl.
| | |
|---|---|
| *G06T 7/70* | (2017.01) |
| *G16H 30/20* | (2018.01) |
| *G16H 50/20* | (2018.01) |
| *G16H 30/40* | (2018.01) |
| *G06N 3/04* | (2006.01) |
| *G06N 3/08* | (2006.01) |
| *G06T 11/00* | (2006.01) |
| *A61B 8/14* | (2006.01) |
| *A61B 8/08* | (2006.01) |

(52) U.S. Cl.
CPC .......... *G06T 11/003* (2013.01); *G16H 30/20* (2018.01); *G16H 30/40* (2018.01); *G16H 50/20* (2018.01); *A61B 8/14* (2013.01); *A61B 8/5207* (2013.01); *G06T 2207/10072* (2013.01); *G06T 2207/10132* (2013.01); *G06T 2207/20081* (2013.01); *G06T 2207/20084* (2013.01)

(56) References Cited

U.S. PATENT DOCUMENTS

| | | | |
|---|---|---|---|
| 2014/0163375 A1* | 6/2014 | Wasielewski | ........ A61B 8/4427 600/443 |
| 2016/0113630 A1 | 4/2016 | Chang et al. | |

FOREIGN PATENT DOCUMENTS

| | | |
|---|---|---|
| JP | 2011524772 | 9/2011 |
| WO | 2009/153723 | 12/2009 |
| WO | 2018048507 | 3/2018 |

OTHER PUBLICATIONS

Preiswerk, Frank, et al., "Synthesizing Dynamic MRI Using Long-Term Recurrent Convolutional Networks," International Conference on Simulation, Modeling, and Programming for Autonomous Robots, Simpar 2010, [Lecture Notes in Computer Science], Springer, Berlin, Heidelberg, Sep. 15, 2018, pp. 89-97, XP047485712, ISBN: 978-3-642-17318-9.

Vedula, Sanketh, et al., "Towards CT-Quality Ultrasound Imaging Using Deep Learning," arxiv.org, Cornell University Library, Ithaca, NY, Oct. 17, 2017, 4 pages, XP080825022.

International Search Report (with English Translation) and Written Opinion of the International Searching Authority, completed Feb. 8, 2019, in International Patent Application No. PCT/EP2018/080495, 13 pages.

Observations on the Written Opinion of the International Searching Authority, Eisenführ Speiser, May 4, 2020, 3 pages.

* cited by examiner

ULTRASOUND IMAGE GENERATING SYSTEM

CROSS-REFERENCE TO RELATED APPLICATIONS

This application is a U.S. national phase of International Patent Application No. PCT/EP2018/080495, filed Nov. 7, 2018; which claims priority from Germany Patent Application No. 10 2017 126 158.3, filed Nov. 8, 2017, which applications are incorporated herein by reference in their entireties.

TECHNICAL FIELD

The invention relates to an ultrasound image generating system, an ultrasound image generating method and a computer program for generating an image of an object using raw ultrasound data.

BACKGROUND

Ultrasonic imaging is used very frequently in medical diagnostics. It is relatively inexpensive and flexible in use. It allows mobile use and provides real-time imaging with up to 50 ultrasound images per second, for example. However, one disadvantage of ultrasound imaging is the relatively low image quality.

An object of the present invention is to provide an ultrasound imaging system, an ultrasound imaging method and a computer program for generating an image of an object, which allow improved image quality to be achieved.

BRIEF DESCRIPTION OF THE DRAWINGS

Embodiments of the invention shall now be described with reference to the attached Figures, in which.

DETAILED DESCRIPTION

Figure 1:
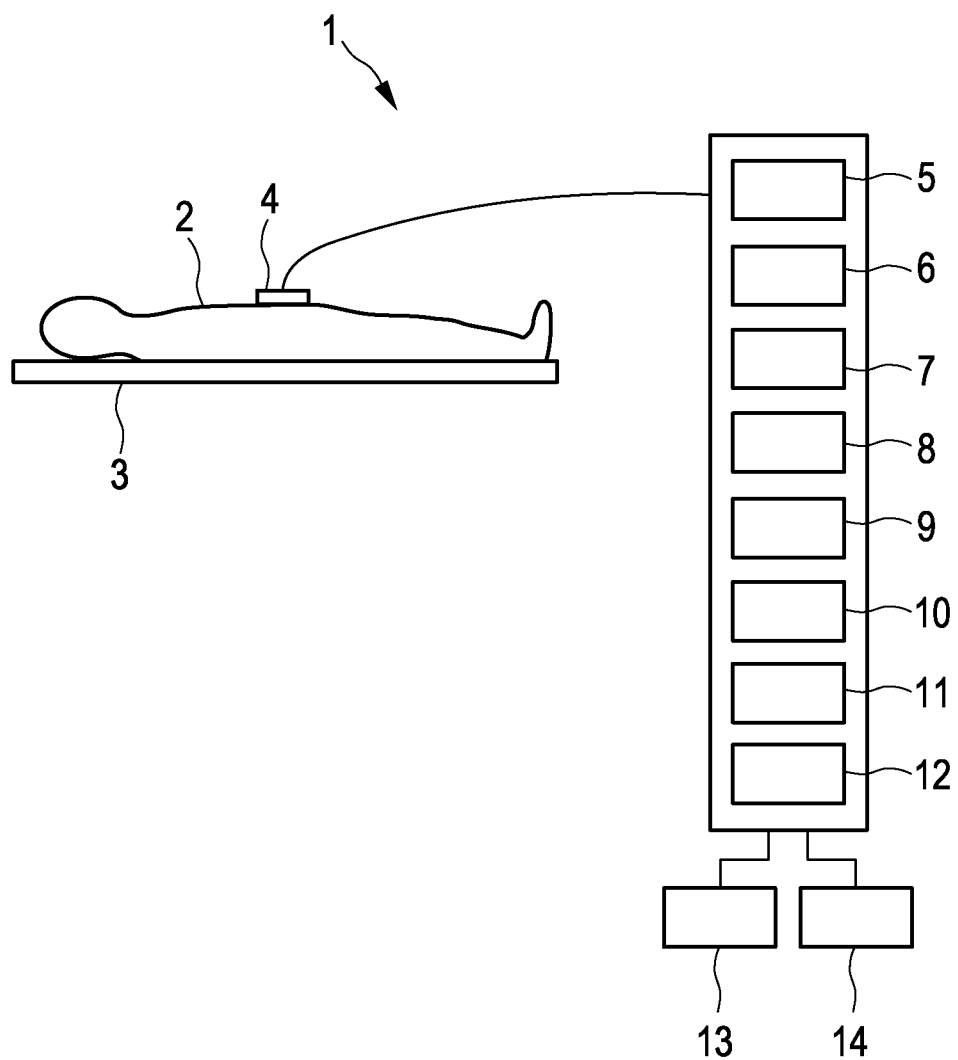
FIG. 1 shows, in schematic form and by way of example, an embodiment of an ultrasound image generating system for generating an image of an object.

This object is achieved by an ultrasound image generating system for generating an image of an object, the ultrasound image generating system comprising:

an ultrasound data provisioning unit for providing raw ultrasound data of the object, which data have been acquired by means of an ultrasound imaging modality, a trained unit provisioning unit for providing a unit trained by machine learning, which is adapted to generate an ultrasound image of an object on the basis of raw ultrasound data of the object, which image does not correspond to the ultrasound imaging modality that was used to acquire the raw ultrasound data, and an image generating unit for generating the image of the object using the provided trained unit, on the basis of the provided raw ultrasound data of the object.

Raw ultrasound data contain a great deal of information about an object, only a very small fraction of which is used by known ultrasound reconstruction techniques. This disregard of a major proportion of the information included in the raw ultrasound data leads, inter alia, to the relatively poor image quality and low contrast of known ultrasound images. However, it is also known how this additional information can be used to improve the image quality.

It has now been discovered that this previously disregarded information included in the raw ultrasound data can be extracted with the aid of a unit trained by machine learning, such as a neural network, that is not used to reconstruct ultrasound images corresponding to the ultrasound imaging modality used to generate the raw ultrasound data. This is, with the aid of the trained unit, it is possible on the basis of the raw ultrasound data to generate ultrasound images which do not correspond to the ultrasound images that can "normally" be generated by means of the ultrasound imaging modality. Instead, the ultrasound images generated by means of the trained unit have characteristics that correspond to a different imaging modality, and the information contained in the raw ultrasound data can be better exploited. By using the trained unit, the ultrasound image generating system can reconstruct an ultrasound image that has the characteristics, for example, of a computed tomography image (CT image), a magnetic resonance image (MR image), a positron emission tomography image (PET image), a single-photon emission computed tomography image (SPECT image) or a magnetic particle image (MPI image). It is also possible to reconstruct a different topographic ultrasound image which does not correspond to the ultrasound imaging modality. The ultrasound image generated by the trained unit differs, therefore, from a "normal" ultrasound image that is normally generated by the ultrasound imaging modality with which the raw ultrasound data were acquired, in that the ultrasound image generated by the trained unit has characteristics of a different imaging modality. By making better use of the information in the raw ultrasound data about the object, the image quality and the information content ("contrast") can be improved.

Each imaging modality basically generates an image that is characteristic of the respective imaging modality. That is, it is known that there are specific image characteristics for each imaging modality, which allow an image to be associated with the respective imaging modality. A CT image, for example, has CT image characteristics, so it is clear to a person skilled in the art that the CT image corresponds to a CT imaging modality. An ultrasound image which does not correspond to the ultrasound imaging modality with which the raw ultrasound data was acquired is an ultrasound image that has image characteristics corresponding to a different imaging modality.

Image characteristics in an image of an object that correspond to an imaging modality which is not the ultrasound imaging modality used to acquire the raw ultrasound data are preferably characteristics of the object shown in the image, which would not be visible in an ultrasound image of the object that would have been generated by means of the ultrasound imaging modality with which the raw ultrasound data were acquired. In the ultrasound image generated by means of the trained unit provided, it may be possible to see, for example, properties of the object that would also be visible in an MR image or in an image produced by some other imaging modality, but not in an ultrasound image produced by the ultrasound imaging modality that was used to acquire the raw ultrasound data.

The trained unit provided by the trained unit provisioning unit uses raw ultrasound data, not ultrasound images, as input. In a known standard reconstruction of an ultrasound image, a large proportion of the object information contained in the raw ultrasound data are lost. This loss of information can be prevented, inter alia by the provided trained unit using the raw ultrasound data as input, and not ultrasound images that have already been reconstructed.

The ultrasound image reconstructed by means of the trained unit provided is still an ultrasound image and generally has typical ultrasound image characteristics, such as speckle patterns or loss of depth resolution. However, this reconstructed ultrasound image also shows characteristics of the object that would not be visible in a "normal" ultrasound image of the ultrasound imaging modality used to acquire the raw ultrasound data, but would be in an MR image, for example, or in a image obtained by a different imaging modality. The imaging modality which is not the ultrasound imaging modality used to acquire the raw ultrasound data and which renders visible the characteristics in the ultrasound image will depend on the imaging modality whose images were used to train the provided unit. For example, if MR images were used to train the unit, the ultrasound image reconstructed by the trained unit will have MR image characteristics, that is, characteristics of the object are visible in the ultrasound image generated by means of the trained unit that are normally not visible in an ultrasound image, but are in an MR image.

Even when the ultrasound image generated by means of the trained unit has MR image characteristics, for example, it is nevertheless, as explained above, an ultrasound image that may have common ultrasound image properties, such as loss of depth resolution. Loss of depth resolution refers, for example, to the ultrasound signal becoming weaker with increasing distance from the ultrasound probe and thus with increasing depth in an object, for example in a patient, due to absorption and scattering, for example, as a result of which the signal-to-noise ratio also decreases with increasing depth.

The ultrasound image may be two-dimensional or three-dimensional, for example. The ultrasound data provisioning unit may be a storage unit in which the raw ultrasound data are stored and which is able to provide the stored raw ultrasound data. However, the ultrasound data provisioning unit may also be a receiver unit that receives the raw ultrasound data and provides the received raw ultrasound data. The ultrasound data provisioning unit may also be the ultrasound imaging modality with which the raw ultrasound data were acquired.

The trained unit provisioning unit may also be a storage unit that provides the trained unit in this case. However, the trained unit provisioning unit may also be a receiver unit which is adapted to receive the trained unit and to provide the received trained unit.

The trained unit is a unit that is adapted by machine learning, i.e., trained, to generate an ultrasound image of an object, which does not correspond to the ultrasound imaging modality, on the basis of raw ultrasound data of the object. That is, the trained unit is a unit that has been trained with raw ultrasound data acquired by the ultrasound imaging modality and with images from a different imaging modality. The trained unit provisioning unit and the trained unit provided are also trained, therefore, by the type of training given to the trained unit. The trained unit provisioning unit is a unit that is adapted to provide a trained unit which has been trained with a) raw ultrasound data acquired by an ultrasound imaging modality and b) images acquired by a different imaging modality. These other images are, for example, CT images, MR images, PET images, SPECT images, MPI images or images from another imaging modality. The trained unit provided has been trained to output those images—when the raw ultrasound data are inputted that were generated by means of the other imaging modality, and as the outputted images are ultrasound images, as explained above, and therefore not exactly the images generated by means of the other imaging modality, this means that training is performed with the aim of outputting these images, an aim that is not achieved, however. In other words, the training is carried out in such a way that differences between the output image generated by the unit to be trained and the respective training image are minimized.

During training, the unit, such as a neural network, is thus trained with the aim of generating an image corresponding to a image from a different imaging modality, for example an MR imaging modality, when the raw ultrasound data acquired by means of an ultrasound imaging modality are inputted. As explained above, the trained unit, which uses the raw ultrasound data as input, will not generate, as its output image, exactly the same MR image as used in this example, but an ultrasound image that has a speckle pattern or loss of depth resolution, for example, but with MR image characteristics that are visible in the MR image. As a result, the trained unit provided is therefore trained, as likewise explained above, in such a way that, despite the aim of outputting the MR image, for example, differences are minimized between the ultrasound image generated by the unit to be trained, on the basis of the raw ultrasound data, and the MR image used for training in this example.

The expression "imaging modality" denotes a respective class of medical appliances used for imaging in medical diagnostics, with different medical appliances of the same imaging modality being identical in the imaging techniques on which they are based. CT is one example of an imaging modality. Another imaging modality is MR, for example. Echo ultrasound is another example of an imaging modality. Yet another imaging modality is transmission ultrasound. PET is another imaging modality. Other imaging modalities are SPECT and MPI.

The ultrasound data provisioning unit is preferably adapted to provide raw ultrasound echo data as raw ultrasound data. This means that an ultrasound echo imaging modality is preferably used to acquire the raw ultrasound data. The ultrasound image, which does not correspond to this ultrasound echo imaging modality, is then an ultrasound image having image characteristics that are not those of an ultrasound echo imaging modality, i.e., of a prior art ultrasound echo imaging modality. The image has, for example, CT image characteristics, MR image characteristics, SPECT image characteristics, PET image characteristics, MPI image characteristics or image characteristics of some other imaging modality. The ultrasound image may also have transmission ultrasound image characteristics that are normally found in images generated by a transmission ultrasound imaging modality. The ultrasound image generated by the trained unit may be a sound-velocity image. The trained unit may be trained to that end with sound-velocity images acquired using a transmission ultrasound imaging modality.

An image characteristic that immediately indicates to a person skilled in the art that the image is an ultrasound image with a CT image characteristic is the characteristically strong contrast between bone and tissue, with bones displayed relatively light and tissue relatively dark. Tissue contrast is a typical image characteristic that immediately indicates to a person skilled in the art that the image is an ultrasound image with an MR image characteristic. A characteristic MR tissue contrast enables distinctions to be made between different types of tissue and between different organs, for example. In head imaging, the MR image characteristic typical of an MR image means that white brain matter can be distinguished very well from gray brain matter. Image characteristics that immediately indicate to a person skilled in the art that the image is an ultrasound image with echo ultrasound image characteristics include speckle patterns, shading along the sound direction, and depth-dependent signal intensity.

When raw ultrasound echo data are used as raw ultrasound data, it is possible by means of the trained unit to generate ultrasound images that have image characteristics of a different imaging modality, with further improvement in image quality and with improved contrast.

Raw ultrasound data are ultrasound data that do not form an ultrasound image. The raw ultrasound data are, for example, directly measured ultrasound data, or ultrasound data that have been processed, for example filtered, without image generation being included in that processing. In particular, raw ultrasound data are measured data from individual elements of an ultrasound receiver array, which may be zero-, one- or two-dimensional. Raw ultrasound data may consist only of the frequency components of the transmitted ultrasound, or may also consist of frequency-shifted ("Doppler shift") components or higher harmonic frequencies generated by nonlinear processes.

Raw ultrasound data may also be generated with additional preparation. This includes tracking shear waves for an ultrasound elastography measurement, or using special transmission pulse shapes and combinations such as pulse inversion or pulse coding.

The trained unit provisioning unit is preferably adapted to provide, as the unit trained by machine learning, a neural network which is adapted to generate an ultrasound image of an object on the basis of raw ultrasound data of the object, which image does not correspond to the ultrasound imaging modality that was used to acquire the raw ultrasound data. In particular, the trained unit provisioning unit is adapted to provide a deep learning network as the neural network. Using a neural deep learning network can result in a further improvement in image quality and to more information content in the image. The trained unit provisioning unit may be adapted to provide a non-fully convolutional neural network (CNN) as the neural network. The result of using such a non-fully convolutional neural network is that generation of the ultrasound image on the basis of the neural network is not based, or not exclusively based, on pattern recognition. This can lead to a further improvement in the quality of the ultrasound image that is generated. The non-fully convolutional neural network has at least one layer that does not perform convolution operations. In one embodiment of the invention, the non-fully convolutional neural network has only one layer that performs convolution operations. In another embodiment, the non-fully convolutional neural network has a plurality of layers that perform convolution operations, the number (first number) of layers that perform convolution operations being less than the number (second number) of layers that do not perform convolution operations. The first number preferably includes 30% or less and more preferably 20% or less of the layers of the non-fully convolutional neural network. Accordingly, the second number preferably includes 70% or more and more preferably 80% or more of the layers of the non-fully convolutional neural network. In addition, in one preferred embodiment, the first number includes only one or two layers of the non-fully convolutional neural network and the second number includes the remaining layers of the non-fully convolutional neural network, i.e., the total number of layers of the non-fully convolutional neural network minus one or minus two. The layers that do not perform any convolution operations may include, for example, fully connected layers and/or restricted Boltzmann machines (RBMs). In one embodiment, the layers that do not perform any convolution operations consist solely of fully connected layers and/or restricted Boltzmann machines (RBMs).

The ultrasound image generating system may also have an image providing unit for providing a further image of the object, which image does not correspond to the ultrasound imaging modality, wherein said further image was not generated using the trained unit. The ultrasound imaging system may also have a registration unit that is adapted to register with each other the further image provided and the ultrasound image generated using the trained unit. The registration unit may be adapted to transform the provided further image in such a way that it is registered with the ultrasound image generated using the trained unit. The further image provided is preferably an image which was previously acquired by means of a different imaging modality and which was stored in a storage unit, said storage unit providing said previously acquired image. This storage unit could therefore be conceived of as an image providing unit. This previously acquired image is, for example, a CT image, an MR image, a PET image, a SPECT image, an MPI image or an image from some other imaging modality that differs from the ultrasound imaging modality that was used to acquire the raw ultrasound data. The previously acquired image, which is preferably not based on raw ultrasound data, but for example on raw CT data or raw MR data, may have an even better image quality than the ultrasound image generated using the trained unit on the basis of raw ultrasound data. By transforming the further image provided, for example the CT image or the MR image, in such a way that it is registered with the ultrasound image generated using the trained unit and the raw ultrasound data, an image of the object can be provided with further improved image quality.

The ultrasound image generating system may have an element identification unit and an indicator generating unit, the element identification unit being adapted to identify the location of an element in the image generated using the trained unit, and the indicator generating unit being adapted to generate an indicator which indicates the location of the element in the further image provided, on the basis of the registration and the identified location. The element, more particularly, may be an interventional instrument, such as a catheter or a needle, and the further image provided may be an image acquired before the interventional instrument was inserted into the body. The further image provided may thus be a pre-interventional image. With the aid of the element identification unit and the indicator generating unit, the interventional instrument can be detected, and segmented, in particular, in the ultrasound image that was generated using the trained unit and the raw ultrasound data and which may be an interventional image, in order to identify the location of the instrument in the body, after which that location can be displayed in the pre-interventional image, which is a CT image or an MR image, for example. This can allow a surgeon to be guided better, for example, while moving the interventional instrument inside the body.

The registration unit is preferably adapted to register an elastic transformation. Using an elastic transformation can result in further improved registration, in particular in a further improved transformation, of the ultrasound image generated using the trained unit and on the basis of the raw ultrasound data. This, in turn, can enable a further improved image quality. The guidance given to a surgeon during an interventional procedure, described above, can also be improved as a result.

The image providing unit and the image generating unit may preferably be adapted such that the further image provided and the ultrasound image generated using the trained unit correspond to the same imaging modality. This means that the ultrasound image generated by means of the trained unit has image characteristics that correspond to the imaging modality with which the further image provided was acquired. In other words, images from an imaging modality with which the further image provided was also acquired were used in this example to train the unit. For example, MR images were used to train the unit and the further image provided is an MR image. This, too, can result in improved registration and thus, for example, in further improved image quality and/or and/or improved guidance for a surgeon during an interventional procedure.

The ultrasound image generating system may have a training unit for training the unit, the training unit being adapted to train the unit such that the trained unit outputs the provided image when the provided raw ultrasound data of the object are inputted. As the outputted images, as explained above, are ultrasound images and therefore not exactly the images generated by a different imaging modality, this means that training is performed with the aim of outputting these images, an aim that is not achieved, however. In other words, the training is carried out in such a way that differences between the output image generated by the unit to be trained and the respective training image are minimized.

The ultrasound image generating system can therefore be used not only to generate an image with CT image characteristics or with MR image characteristics, for example on the basis of raw ultrasound data, but also to train the trained unit further. This further training may result in an improved unit trained by machine learning and thus to a further improved image quality, for example of the images, generated on the basis of the raw ultrasound data, with CT image characteristics or MR image characteristics.

The training unit tries, therefore, to train the unit so that the trained unit outputs the respective provided image from a different imaging modality, for example an MR image, when the provided raw ultrasound data of the object are inputted. Although the training is performed with that objective, the ultrasound image generated by the trained unit will be different, for example, from an MR image used for training purposes, as described above. This difference is due, for example, to the fact that the ultrasound image generated by the trained unit may have ultrasound image characteristics such as the aforementioned loss of depth resolution. The training unit is adapted to train the unit such that differences are minimized between the ultrasound image generated by the trained unit and the image from a different imaging modality used for training, so as to generate an ultrasound image that corresponds as well as possible to the image from the other imaging modality used for training.

The aforementioned object is also achieved by a training system for training a unit by machine learning, wherein the training system comprises:

an ultrasound data provisioning unit for providing raw ultrasound data of an object, which have been acquired by means of an ultrasound imaging modality or which have been generated by simulating acquisition by means of the ultrasound imaging modality, a unit-to-be-trained provisioning unit for providing a unit to be trained by machine learning, an image providing unit for providing an image of the object which has not been acquired by means of the ultrasound imaging modality with which the raw ultrasound data were acquired, and which has not been generated by simulating acquisition by means of the ultrasound imaging modality, a training unit for training the provided unit-to-be-trained, such that the trained unit outputs the provided image when the provided raw ultrasound data of the object are inputted. As the outputted images, as explained above, are ultrasound images and therefore not exactly the images generated by a different imaging modality, this means that training is performed with the aim of outputting these images, an aim that is not achieved, however. In other words, the training is carried out in such a way that differences between the output image generated by the unit to be trained and the respective training image are minimized.

As already noted in the foregoing, the training unit is configured in such a way that differences are minimized between the ultrasound image generated by the trained unit and the image provided, which for example is an MR image. The trained unit optimized in this manner will then generate an ultrasound image, on the basis of raw ultrasound data, which has characteristics of the imaging modality with which the provided image used for training was generated.

The image providing unit may be a storage unit in which the image of the object is stored and which is adapted to provide the stored image. The image providing unit may also be a receiver unit adapted to received the image and to provide the received image. Furthermore, the image providing unit may also be a measurement unit or acquisition unit that is adapted to acquire the image and to provide the acquired image. For example, the image providing unit may be a CT system or an MR system. The provided image is, for example, a CT image, an MR image or an image from some other imaging modality that is not the imaging modality with which the raw ultrasound data were acquired, for example a PET image, a SPECT image or an MPI image.

It is preferred that the ultrasound data provisioning unit and the image providing unit are adapted to acquire, in particular simultaneously, the raw ultrasound data and the image of a same area of the object. By simultaneously acquiring the raw ultrasound data and the provided image, and using this simultaneously acquired raw ultrasound data and image to train the unit, for example a neural network, it is possible to prevent any deterioration in the quality of the training given to the unit due to movements of the object. This can result in an improved and ultimately trained unit and thus in a further improved image quality when the trained unit is used to generate an ultrasound image with MR image characteristics, for example, on the basis of raw ultrasound data.

It is also preferred that the training unit is adapted a) to firstly generate an ultrasound image of the object, in particular an ultrasound tomography image, on the basis of the raw ultrasound data provided, b) to then train the unit such that the trained unit outputs the generated ultrasound image when the provided raw ultrasound data of the object are inputted, and finally c) to train the unit such that when the provided raw ultrasound data of the object are inputted, the trained unit outputs the image that was provided by the image providing unit, and which is a tomography image, in particular. As the outputted images, as explained above, are ultrasound images and therefore not exactly the images generated by a different imaging modality, this means that training is performed with the aim of outputting these images, an aim that is not achieved, however. In other words, the training is carried out in such a way that differences between the output image generated by the unit to be trained and the respective training image are minimized.

The unit may therefore be trained in two steps, with the geometric mapping being trained in a first step and the contrast mapping in a second step, that is, mapping from the ultrasound imaging modality to a different imaging modality. This two-step process may result in a further improved trained unit and thus, when the trained unit is used to generate images, to a further improved quality of the ultrasound image generated on the basis of raw ultrasound data, for example with CT image characteristics or MR image characteristics. This two-step process may also result in training success being achieved faster.

The ultrasound data provisioning unit may be adapted to provide raw ultrasound echo data and raw ultrasound transmission data as raw ultrasound data. The training unit can also be adapted a) to firstly generate an ultrasound tomography image of the object on the basis of the raw ultrasound transmission data provided, without using the unit to be trained in that respect, b) to then train the unit such that the trained unit outputs the generated ultrasound tomography image when the raw ultrasound transmission data provided are inputted, and finally c) to train the unit such that the trained unit outputs the image provided by the image providing unit when the provided raw ultrasound echo data of the object are inputted, the provided image preferably being a tomography image, and as the outputted images are ultrasound images, as explained above, and therefore not exactly the images generated by means of the other imaging modality, this means here as well that training is performed with the aim of outputting these images, an aim that is not achieved, however. In other words, the training is carried out in such a way that differences between the output image generated by the unit to be trained and the respective training image are minimized.

Generation of the ultrasound tomography image on the basis of the raw ultrasound transmission data may be, for example, a known reconstruction which uses only the ultrasound transmission data, in particular. However, generation of the ultrasound tomography image on the basis of the raw ultrasound transmission data may also be a reconstruction that additionally uses the raw ultrasound echo data, the raw ultrasound transmission data being used to determine the sound velocity, in particular a sound velocity map, inside the object, the ultrasound tomography image then being reconstructed in a known manner by means of the raw ultrasound echo data, taking the determined sound velocity into consideration.

The training of the trained unit can be further improved if, during the two-step training, the geometric mapping is already trained in the first step with an ultrasound tomography image, and if the contrast transmission is trained in the second step with a provided tomographic image, i.e., if tomographic images are used for training in both steps. This, in turn, may finally result in further improved image quality, if the improved trained unit is used, for example, to generate an ultrasound image with CT image characteristics or MR image characteristics on the basis of raw ultrasound data.

The aforementioned object is also achieved by a unit trained by machine learning, which is adapted to generate an ultrasound image of an object on the basis of raw ultrasound data of the object, which image does not correspond to the ultrasound imaging modality that was used to acquire the raw ultrasound data.

The aforementioned object is also achieved by an ultrasound image generating method for generating an image of an object, the ultrasound image generating method comprising the steps of:
providing raw ultrasound data of the object, which have been acquired by means of an ultrasound imaging modality, by means of an ultrasound data provisioning unit,
providing, by means of a trained unit provisioning unit, a unit trained by machine learning, which is adapted to generate an ultrasound image of an object on the basis of raw ultrasound data of the object, which image does not correspond to the ultrasound imaging modality with which the raw ultrasound data were acquired, and
generating the image of the object using the provided trained unit, on the basis of the provided raw ultrasound data of the object, by means of an image generating unit.

The aforementioned object is also achieved by a training method for training a unit by machine learning, said training method comprising the steps of:
providing raw ultrasound data of an object by means of an ultrasound data provisioning unit, which have been acquired by means of an ultrasound imaging modality or which have been generated by simulating acquisition by means of the ultrasound imaging modality,
providing a unit-to-be-trained by means of a trained unit provisioning unit,
providing an image of the object by means of an image providing unit, which image has not been acquired by means of the ultrasound imaging modality with which the raw ultrasound data were acquired, and which has not been generated by simulating acquisition by means of the ultrasound imaging modality,
training, by means of a training unit, the provided unit-to-be-trained, such that the trained unit outputs the provided image when the provided raw ultrasound data of the object are inputted, and as the outputted images are ultrasound images, as explained above, and therefore not exactly the images generated by means of the other imaging modality, this means that training is performed with the aim of outputting these images, an aim that is not achieved, however. In other words, the training is carried out in such a way that differences between the output image generated by the unit-to-be-trained and the respective training image are minimized.

The aforementioned object is also achieved by a computer program for generating an image of an object, wherein the computer program is adapted to carry out the ultrasound image generating method according to claim 15 when it is run on an ultrasound image generating system for generating images in accordance with any one of claims 1 to 8.

The aforementioned object is also achieved by a computer program for training a unit by machine learning, wherein the computer program is adapted to carry out the training method for training a unit by machine learning in accordance with claim 15 when it is run on a training system for training a unit by machine learning in accordance with any one of claims 9 to 13.

It should be understood that the ultrasound image generating system according to claim 1, the training system according to claim 9, the ultrasound image generating system according to claim 15, the training method according to claim 16 and the computer program according to claims 17 and 18 have similar and/or identical preferred embodiments, as defined in particular in the dependent claims.

An embodiment of an ultrasound image generating system for generating an image of a patient is shown in schematic form and by way of example in FIG. 1. The ultrasound image generating system 1 comprises an ultrasound measuring device 4, that is, an ultrasound imaging modality, and a control unit 5 for controlling the ultrasound measuring device 4. With the aid of ultrasound measuring device 4 and control unit 5, a physician, for example, can acquire raw ultrasound data of the patient 2 who is lying on a patient couch 3. In this embodiment, ultrasound measuring device 4 and control unit 5 are adapted to acquire raw ultrasound echo data.

Ultrasound measuring device 4 may be a hand-held device, for example, that is held in the physician's hand during acquisition of the raw ultrasound data. However, the ultrasound measuring device may also be a stationary measuring device. After being placed on the patient 2 by a physician, for example, the ultrasound measuring device can also be released so that it is not held in the hand during the acquisition of the raw ultrasound data.

As raw ultrasound data can be provided by ultrasound measuring device 4 and control unit 5, ultrasound measuring device 4 and control unit 5 may be conceived of as components of an ultrasound data provisioning unit for providing raw ultrasound data of patient 2.

The ultrasound image generating system 1 also comprises a trained unit provisioning unit 6 for providing a unit generated by machine learning, which in this example is a neural network which is adapted to generate, on the basis of raw ultrasound data of a patient, an image of the patient that does not correspond to ultrasound echo imaging modality 4. In this example, the trained unit provisioning unit may also be referred to, therefore, as a neural network provisioning unit. In this embodiment, the trained unit provisioning unit 6 is adapted to generate, on the basis of raw ultrasound data, an ultrasound image with MR image characteristics, for example with T1-weighted MR image characteristics, wherein the neural network is a deep learning network, in particular a non-fully convolutional neural network. The ultrasound image generating system 1 also comprises an image generating unit 7 for generating the ultrasound image of patient 2 with MR image characteristics, using the provided neural network and on the basis of the measured raw ultrasound data.

The ultrasound image generating system 1 also comprises, preferably, an image providing unit 8 for providing a further image of the patient 2 which does not correspond to ultrasound echo imaging modality 4, wherein the image was not generated using the neural network. In this embodiment, image providing unit 8 is adapted to provide an MR image of the patient that was previously generated, for example a few days previously, with the aid of known reconstruction algorithms on the basis of raw MR data of the patient. These known reconstruction algorithms include, for example, a Fourier transform from a k domain to a spatial domain. This previously acquired MR image can be registered by means of a registration unit 9 with the image generated by image generating unit 7, wherein the previously acquired MR image can be transformed by means of an elastic transformation, in particular. A transformed, previously acquired MR image can thus be created by registration with the image generated by imaging generating unit 7.

The ultrasound image generating system 1 may also have an element identification unit 10 which is adapted to identify a location of an element in the ultrasound image with MR image characteristics that was generated using the neural network. To that end, element identification unit 10 can use known segmentation algorithms, for example, and the element is an interventional instrument, for example, that is used during a surgical procedure.

This interventional instrument can be detected in the ultrasound image with MR image characteristics that was generated on the basis of the raw ultrasound data, in order to locate the interventional instrument within that image. By registering this ultrasound image with MR image characteristics with the previously acquired MR image generated on the basis of on the basis of raw MR data, the location of the interventional instrument can also be shown in the previously acquired MR image. If the previously acquired MR image has a better image quality than the ultrasound image with MR image characteristics that was generated on the basis of the raw ultrasound data, then displaying the location of the interventional instrument in the "real" MR image generated on the basis of the raw MR data can improve the guidance given to a surgeon moving the interventional instrument inside patient 2.

To display the location of the interventional instrument in the MR image that was previously generated on the basis of the raw MR data, an indicator generating unit 11 can be used that is adapted to generate, on the basis of the registration and the determined location, an indicator showing the location of the interventional Instrument in the previously acquired MR image acquired pre-interventionally on the basis of raw MR data.

The ultrasound image generating system 1 further comprises a training unit 12 for training the neural network such that the trained neural network outputs the MR image generated by image providing unit 8 when the provided raw ultrasound data of the patient are inputted. In other words, the ultrasound image generating system 1 may be adapted not only to generate an ultrasound image with MR image characteristics, for example, on the basis of raw ultrasound data and by using the neural network, but may also be adapted to train the neural network further in order to improve it further. The training unit tries to train the neural network in such a way that the MR image is outputted when the raw ultrasound data is inputted. It is clear that this is possible only to approximate extent, however, as the image generated by the neural network is an ultrasound image. Training unit 12 is therefore adapted to train the neural network in such a way that differences between the ultrasound image generated by means of the neural network, and the MR image are minimized. The expression "training the neural network in such a way that the trained neural network output the MR image [ . . . ] when the provided raw ultrasound data are inputted" therefore means that training unit 12 trains the neural network with that aim, by minimizing the respective differences, whereby the ultrasound image outputted by the neural network that is eventually trained is not exactly the same as the MR image, but matches it as well as possible.

The ultrasound image generating system 1 further comprises an input unit 13, for example a keyboard, a computer mouse, a touch-sensitive display, etc., and an output unit 14, for example a monitor. The ultrasound image generating system 1 is adapted, in particular, to display the image generated by image generating unit 7. Other images can also be displayed on output unit 14, for example the transformed, previously acquired MR image mentioned above. The previously acquired MR image with the indicator showing the location of the interventional instrument can also be displayed on output unit 14.

Figure 2:
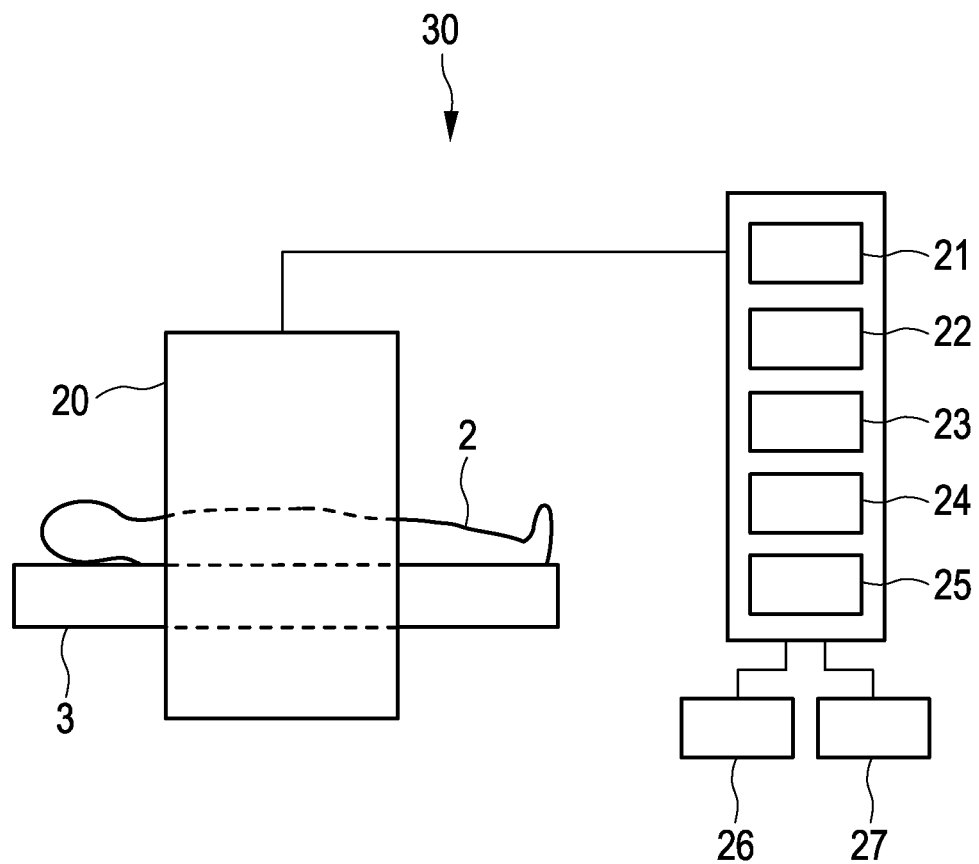
FIG. 2 shows, in schematic form and by way of example, an embodiment of a training system for training a neural network.

An embodiment of a training system for training a neural network is shown in schematic form and by way of example in FIG. 2.

Training system 30 includes a raw data acquisition unit 20 for acquiring raw MR data, raw ultrasound echo data and raw ultrasound transmission data. Training system 30 also includes an MR control and reconstruction unit 21 to control the acquisition of the raw MR data and for reconstructing an MR image on the basis of the raw MR data. Training system 30 also includes an ultrasound control unit 22 for controlling the acquisition of the raw ultrasound echo data and the raw ultrasound transmission data, and an ultrasound reconstruction unit 23 for reconstructing an ultrasound tomography image on the basis of the raw ultrasound transmission data and the raw ultrasound echo data, the raw ultrasound transmission data being used to determine the sound velocities inside the patient and these sound velocities then being taken into account when reconstructing the ultrasound tomography image with the aid of the raw ultrasound echo data. Ultrasound reconstruction unit 23 is preferably configured to reconstruct the ultrasound tomography image without using a neural network. It preferably uses known ultrasound tomography reconstruction algorithms instead. However, it may also be adapted to use a neural network for reconstruction. It is also preferable that the MR control and reconstruction unit 21 does not use a neural network to reconstruct the MR image on the basis of the raw MR data, but known MR reconstruction algorithms based, for example, on a Fourier transform from a k domain to a spatial domain. However, it may also be adapted to use a neural network for reconstruction.

As raw data acquisition unit 20 is adapted to acquire raw ultrasound echo data and raw ultrasound transmission data, with this acquisition of raw data being controlled by ultrasound control unit 22, raw data acquisition unit 20 and ultrasound control unit 22 may be conceived of as components of an ultrasound data provisioning unit for providing raw ultrasound data of patient 2. As raw data acquisition unit 20 also acquires raw MR data, and MR control and reconstruction unit 21 reconstructs an MR image of patient 2 on the basis of those raw MR data, raw data acquisition unit 20 and MR control and reconstruction unit 21 may be conceived of as components of an image providing unit for providing an image of patient 2 that does not correspond to the ultrasound imaging modality. Raw data acquisition unit 20, MR control and reconstruction unit 21 and ultrasound control unit 22 are adapted such that the raw MR data, the raw ultrasound echo data and the raw ultrasound transmission data are acquired simultaneously from a same region of patient 2.

Training system 30 further comprises a unit-to-be-trained provisioning unit 24 for providing a neural network to be trained, and a training unit 25 for training the provided neural network such that the trained neural network outputs the reconstructed MR image when the measured raw ultrasound echo data of patient 2 are inputted. As the unit to be trained is a neural network, in the examples described here, the unit-to-be-trained provisioning unit 24 may also be conceived of as a neural network provisioning unit. Training unit 25 is preferably adapted to perform this training of the neural network in two steps. In a first step, the neural network is trained in such a way that the trained neural network outputs the reconstructed ultrasound tomography image when the raw ultrasound transmission data of patient 2 are inputted. After this training, the neural network is trained in such a way in a second step that the neural network outputs the reconstructed MR image reconstructed by MR control and reconstruction unit 21, when the measured raw ultrasound echo data of patient 2 are inputted.

It should be noted here also that, although training unit 25 trains the provided neural network with the aim of outputting the reconstructed MR image when the measured raw ultrasound echo data of patient 2 are inputted, that aim is not exactly achieved, because the image generated by means of the neural network is an ultrasound image and not an MR image. However, training with the aim that the neural network outputs the reconstructed MR image has the result that the ultrasound image generated by means of the trained neural network matches the reconstructed MR image as well as possible and in particular that MR image characteristics of the object are visible in the ultrasound image generated by means of the neural network. Training unit 25 trains the provided neural network in such a way that differences between the ultrasound image generated by means of the neural network and the reconstructed MR image are minimized. In other words, the attempt is made to keep the differences between the MR image and the ultrasound image generated by the trained neural network as small as possible.

The neural network is trained using a large number of training sets, each training set comprising raw ultrasound data and an MR image of a patient.

Training system 30 further comprises an input unit 26, such as a keyboard, a computer mouse, a touch-sensitive display, etc., and an output unit 27, for example a monitor.

Raw data acquisition unit 20 includes, for example, holders for ultrasound probes for acquiring raw ultrasound echo data and raw ultrasound transmission data, and these ultrasound probes. Raw data acquisition unit 20 also includes an MR system, to which the holders with the ultrasound probes are attached. The holders may also be attached to patient couch 3. Liquid-filled markers on the ultrasound probes may be used to measure the position and orientation of the respective ultrasound probe in MR images. The two coordinate systems of the MR system and the ultrasound probes have thus been registered. Alternatively, other tracking systems based on other tracking techniques may be used, such as optical tracking systems.

Figure 3:
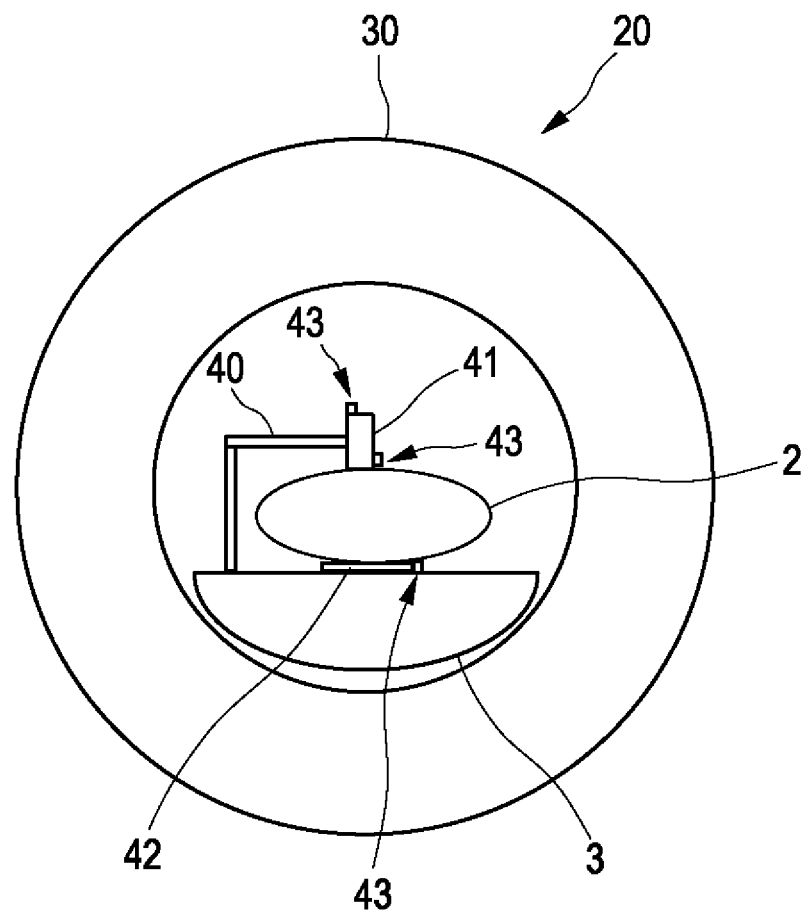
FIG. 3 shows, in schematic form and by way of example, details of a raw data acquisition unit of the training system.

Raw data acquisition unit 20 is illustrated in somewhat more detail in FIG. 3. Raw data acquisition unit 20 includes an MR raw data acquisition unit 30, ultrasound transceiver 41 and an ultrasound receiver 42 for acquiring the raw ultrasound data. To acquire the raw ultrasound transmission data, ultrasound transceiver 41 is operated as an ultrasound transmitter, the transmitted ultrasound waves being received by ultrasound receiver 42. Ultrasound transceiver 41 and ultrasound receiver 42 are arranged in such a way that the transmitted ultrasound waves pass through patient 2 before being received by ultrasound receiver 42. In this embodiment, ultrasound transceiver 41 is arranged by means of a holder 40 above patient 2, and ultrasound receiver 42 is integrated into patient couch 3. Ultrasound receiver 42 is preferably integrated into patient couch 3 in such a way that ultrasound receiver 42 does not cause any protrusion on the top surface of patient couch 3. In particular, ultrasound receiver 42 is preferably recessed into patient couch 3 and is arranged, for example, behind a cover and invisible to the patient.

MR markers 43 may be mounted on ultrasound transceiver 41 and on ultrasound receiver 42 in order to identify the position and orientation of ultrasound transceiver 41, 42 in a coordinate system defined by MR raw data acquisition unit 30. This may ensure that the raw ultrasound echo data, the raw ultrasound transmission data and the raw MR data all relate to the same region of patient 2. The respective registration may be carried out by ultrasound control unit 22, for example, or by MR control and reconstruction unit 21. MR markers 43 are filled with a liquid such as water, for example, to make them visible in an MR image.

Figure 4:
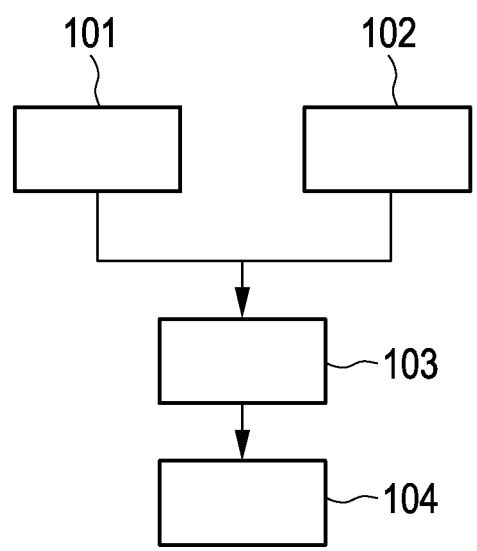
FIG. 4 shows a flow diagram illustrating an embodiment of an ultrasound image generating method for generating an image of an object.

In the following, an embodiment of an ultrasound image generating method for generating an image of an object shall be described by way of example with reference to a flow diagram that is shown in FIG. 4.

In step 101, raw ultrasound data of patient 2 are provided by means of ultrasound data provisioning unit 4, 5. Raw ultrasound echo data are measured, in particular, by ultrasound measuring device 4, which is controlled by means of control unit 5.

In step 102, the neural network is provided that has been trained in such a way that, on the basis of raw ultrasound echo data, an ultrasound image is generated that does not correspond to the ultrasound imaging modality. In particular, the neural network is trained in such a way that, on the basis of raw ultrasound echo data, an ultrasound image with MR image characteristics is generated.

In step 103, an image of patient 2 is generated by image generating unit 7, using the neural network provided in step 102, on the basis of the raw ultrasound echo data provided in step 101. That means, in particular, that an ultrasound image of the patient, with MR characteristics, is generated on the basis of the raw ultrasound echo data measured by ultrasound measuring device 4 and using the neural network. In step 104, the image generated in this manner is displayed on output unit 14.

Figure 5:
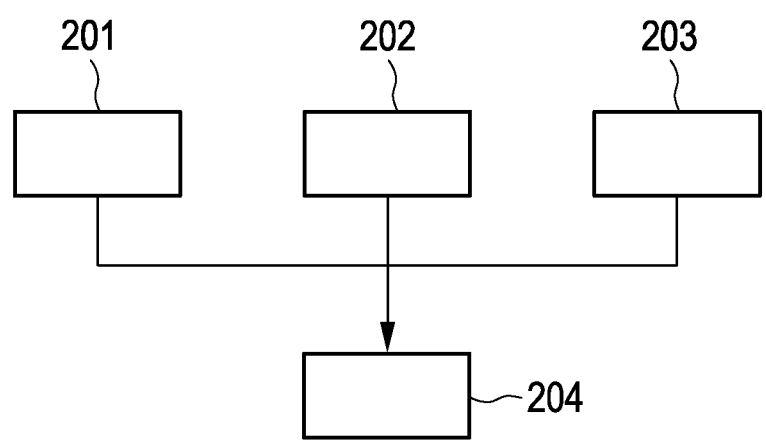
FIG. 5 shows a flow diagram illustrating an embodiment of a training method for training a neural network.

In the following, an embodiment of a training method for training a neural network shall be described by way of example with reference to a flow diagram that is shown in FIG. 5.

In step 201, raw ultrasound data of patient 2 are provided by means of ultrasound data provisioning unit 20, 22. In particular, raw ultrasound echo data and raw ultrasound transmission data are acquired simultaneously by raw data acquisition unit 20, which is controlled by ultrasound control unit 22. In step 202, an image of patient 2 is provided by image providing unit 20, 21. That means, in particular, that raw MR data are measured by raw data acquisition unit 20 simultaneously with the measuring of the raw ultrasound echo data and the raw ultrasound transmission data. The raw MR data are then reconstructed to form an MR image.

In step 203, a neural network is provided by trained unit provisioning unit 24, and in step 204 training unit 25 trains the provided neural network in such a way that the trained neural network outputs the provided image when the provided raw ultrasound data of patient 2 are inputted. This means that training unit 25 trains the provided neural network with the aim that the trained neural network outputs the provided image when the provided raw ultrasound data of patient 2 are inputted. However, since the image outputted by the trained neural network is an ultrasound image, it will not match the provided image one-to-one, as noted above. Training unit 25 nevertheless trains the provided neural network with the described aim by trying to minimize differences between the ultrasound image generated by the trained neural network and the provided image. This training can be carried out in two steps, and the raw ultrasound transmission data and the raw ultrasound echo data can be used to reconstruct an ultrasound tomography image without using the neural network, after which the neural network is then trained in a first step in such a way that the trained neural network outputs the reconstructed ultrasound tomography image when the raw ultrasound echo data are inputted. In a second step, the network is trained further such that the reconstructed MR image is outputted when the raw ultrasound echo data are inputted.

Although the image generated by the neural network in the above embodiments has MR image characteristics, the neural network may also be trained to generate, on the basis of the raw ultrasound data, ultrasound images with image characteristics of a different imaging modality, for example an ultrasound image with CT image characteristics, an ultrasound image with PET image characteristics, an ultrasound image with SPECT image characteristics or an ultrasound image with MPI image characteristics.

When the neural network is configured to generate, on the basis of the raw ultrasound data, an ultrasound image with MR image characteristics, the ultrasound image may have image characteristics of a specific MR contrast. In other words, the neural network may be trained to generate, on the basis of the raw ultrasound data, an ultrasound image with MR image characteristics which has a desired contrast, which means a desired tissue-specific contrast, in particular. The image may have T1 image characteristics, T2 image characteristics, T2* image characteristics, proton density image characteristics, perfusion image characteristics, fat content image characteristics, diffusion image characteristics, flow image characteristics, motion image characteristics, magnetization transfer image characteristics image characteristics, chemical exchange saturation transfer image characteristics, etc.

The ultrasound image generating system may also be adapted to provide a plurality of neural networks, each trained to generate an ultrasound image having image characteristics of a different imaging modality and/or of a different contrast type of the same imaging modality. The ultrasound image generating method may also have a selector unit that allows a user to select which imaging modality to which the ultrasound image to be generated is to correspond. The user is thus able to select an appropriate neural network which is then used to generate images on the basis of the raw ultrasound data.

Once the neural network has been trained, it allows an ultrasound image, for example an ultrasound image with CT image characteristics or with MR image characteristics, to be generated very quickly purely on the basis of the raw ultrasound data. Since the raw ultrasound data can also be acquired very quickly, i.e., at 50 images per second, for example, the ultrasound image generating system may be used to acquire, over a certain period of time and with a very high time resolution, ultrasound images with CT image characteristics, MR image characteristics, or ultrasound images corresponding to a different imaging modality which is not the ultrasound imaging modality that was used to acquire the raw ultrasound data, in order to monitor a movement very precisely, for example. This allows ultrasound images, for example with CT image characteristics or MR image characteristics, to be provided in real time.

Although measured data are used in the embodiments described above to train the neural network, it is also possible to use simulated data for training, in particular simulated raw ultrasound data and/or images based on a simulation. These simulated data are idealized data that, for example, do not contain image artifacts, which real images may contain. By using these simulated data, the quality of neural network training can be further improved, which can ultimately lead to a further improvement in the generation, for example, of an ultrasound image with CT image characteristics or an ultrasound image with MR image characteristics, using the trained neural network on the basis of the raw ultrasound data. A combination of measured data and simulated data may also be used for training.

Although the training was carried out in two steps, in the embodiments described above, the training may also be carried out in one step, for example, the neural network then being trained in such a way that the neural network outputs the provided image from a different imaging modality, for example an MR image that was reconstructed by the MR control and reconstruction unit 21, when the raw ultrasound data of the patient are inputted. The first step of the two-step training scheme described in the embodiments above can therefore be omitted.

Although reference is made, in the embodiments above, to medical imaging, the imaging and training based on ultrasound may also be used in other areas such as materials research or ultrasound microscopy. The patient may be a human or animal patient. The ultrasound image generating system and the training system may also be used for technical objects.

Although the unit to be trained and the trained unit are neural networks, in the embodiments above, these units may also be other units that are or have been trained by machine learning. These units may be hidden Markov models, systems for supervised dictionary learning, Hebbian learning or gradient descent learning.

In the claims, the words "comprise" and "include" do not exclude other elements or steps, and the indefinite article "a/an" does not exclude a plurality.

A single system, a single unit or a single device may perform the functions of several elements mentioned in the claims. The fact that individual functions and elements are mentioned in different dependent claims does not mean that a combination of these functions or elements could not also be used to advantage.

Operations such as providing raw ultrasound data, providing the neural network, generating an image, etc., that are carried out by one or more units or devices, can also be carried out by a different number of units or devices. These operations and/or control of the ultrasound image generating system in accordance with the ultrasound image generating method and/or control of the training system in accordance with the training method may be implemented as program code of a computer program and/or as corresponding hardware.

A computer program may be stored and/or distributed on a suitable medium, for example on an optical storage medium or a solid-state storage medium which is operated in combination with or as part of other hardware. However, the computer program may also be distributed in other forms, for example via the Internet or other telecommunications systems.

The reference signs in the claims are not to be understood as meaning that the subject-matter and the extent of protection conferred by the claims are limited by these reference signs.

The invention claimed is:

1. An ultrasound image generating system for generating an image of an object, comprising:
   an ultrasound data provisioning unit configured to provide raw ultrasound data of the object, the raw data having been acquired using an ultrasound imaging modality, wherein the raw ultrasound data are ultrasound data that do not form an ultrasound image;
   a trained unit provisioning unit configured to provide a unit trained by machine learning, that is further configured to generate an ultrasound image of an object based on raw ultrasound data of the object, wherein the generated image does not correspond to the ultrasound imaging modality that was used to acquire the raw ultrasound data; and
   an image generating unit configured to generate the image of the object using the provided trained unit, based on the provided raw ultrasound data of the object.

2. The ultrasound image generating system of claim 1 wherein the ultrasound data provisioning unit is further configured to provide raw ultrasound echo data acquired using an ultrasound echo imaging modality as the raw ultrasound data.

3. The ultrasound image generating system of claim 1 wherein the trained unit provisioning unit is further configured to provide, as the trained unit, a trained unit configured to generate an image of an object based on raw ultrasound data of the object, with image characteristics selected from a group consisting of: computed tomography image characteristics, magnetic resonance image characteristics, positron emission tomography image characteristics, single-photon emission computed tomography image characteristics and magnetic particle image characteristics.

4. The ultrasound image generating system of claim 1 wherein the trained unit provisioning unit is further configured to provide, as the unit trained by machine learning, a neural network that is configured to generate an ultrasound image of an object based on raw ultrasound data of the object, wherein the generated image does not correspond to the ultrasound imaging modality that was used to acquire the raw ultrasound data.

5. The ultrasound image generating system of claim 4 wherein the trained unit provisioning unit is configured to provide a non-fully convolutional neural network as the neural network.

6. The ultrasound image generating system of claim 1 wherein the ultrasound image generating system has an image providing unit configured to provide a further image of the object, wherein the further image does not correspond to the ultrasound imaging modality, and wherein the further image was not generated using the trained unit.

7. The ultrasound image generating system of claim 6 wherein the ultrasound image generating system has a registration unit configured to register with each other the further image provided and the image generated using the trained unit.

8. The ultrasound image generating system of claim 7 wherein the ultrasound image generating system comprises:
   an element identification unit for identifying the location of an element in the image generated using the trained unit; and
   an indicator generating unit for generating an indicator which indicates the location of the element in the further image provided, based on the registration and the identified location.

9. A training system for training a unit by machine learning, comprising:
   an ultrasound data provisioning unit configured to provide raw ultrasound data of an object, the raw data having been acquired using an ultrasound imaging modality or having been generated by simulating acquisition using the ultrasound imaging modality, wherein the raw ultrasound data are ultrasound data that do not form an ultrasound image;
   a unit-to-be-trained provisioning unit configured to provide a unit to be trained by machine learning;

an image providing unit configured to provide an image of the object that has not been acquired by means of the ultrasound imaging modality with which the raw ultrasound data were acquired, and that has not been generated by simulating acquisition using the ultrasound imaging modality; and a training unit for training the provided unit-to-be-trained, such that the trained unit outputs the provided image when the provided raw ultrasound data of the object are inputted.

10. The training system of claim 9 wherein the ultrasound data provisioning unit and the image providing unit are further configured to acquire the raw ultrasound data and the image of a same area of the object.

11. The training system of claim 9 wherein the training unit is further configured a) to firstly generate an ultrasound image of the object based on the raw ultrasound data provided, b) to train the unit-to-be-trained such that the trained unit outputs the generated ultrasound image when the provided raw ultrasound data of the object are inputted, and c) to train the unit such that when the provided raw ultrasound data of the object are inputted, the trained unit outputs the image provided by the image providing unit.

12. The training system of claim 9 wherein the ultrasound data provisioning unit is configured to provide raw ultrasound echo data and raw ultrasound transmission data as raw ultrasound data.

13. The training system of claim 12 wherein the training unit is further configured a) to firstly generate an ultrasound tomography image of the object based on the raw ultrasound transmission data provided, b) to train the unit such that the trained unit outputs the generated ultrasound tomography image when the raw ultrasound transmission data provided are inputted, and c) to train the unit such that the trained unit outputs the image provided by the image providing unit when the provided raw ultrasound echo data of the object are inputted.

14. A unit trained by machine learning wherein the unit is configured to generate an ultrasound image of an object based on raw ultrasound data of the object, wherein the generated image does not correspond to the ultrasound imaging modality that was used to acquire the raw ultrasound data, wherein the raw ultrasound data are ultrasound data that do not form an ultrasound image.

15. An ultrasound image generating method for generating an image of an object, comprising:

providing raw ultrasound data of the object wherein the raw data has been acquired using an ultrasound imaging modality of an ultrasound data provisioning unit, wherein the raw ultrasound data are ultrasound data that do not form an ultrasound image;

providing, using a trained unit provisioning unit a unit trained by machine learning, the trained unit configured to generate an ultrasound image of an object based on raw ultrasound data of the object, wherein the generated image does not correspond to the ultrasound imaging modality used to acquire the raw ultrasound data; and generating the image of the object using an image generating unit and the provided trained unit and based on the provided raw ultrasound data of the object.

16. A training method for training a unit by machine learning, comprising:

providing raw ultrasound data of an object using an ultrasound data provisioning unit, the raw data having been acquired using an ultrasound imaging modality or having been generated by simulating acquisition using the ultrasound imaging modality, wherein the raw ultrasound data are ultrasound data that do not form an ultrasound image;

providing a unit-to-be-trained using a trained unit provisioning unit;

providing an image of the object using an image providing unit, wherein the provided image has not been acquired using the ultrasound imaging modality used to acquire the raw ultrasound data, and has not been generated by simulating acquisition using the ultrasound imaging modality; and training, using a training unit, the provided unit-to-be-trained, such that the trained unit outputs the provided image when the provided raw ultrasound data of the object are inputted.

17. A non-transitory computer-readable storage medium containing instructions for controlling a computer processor, when executed, to generate an image of an object by performing the ultrasound image generating method of claim 15 when executed on the ultrasound image generating system of claim 1.

18. A non-transitory computer-readable storage medium containing instructions for controlling a computer processor, when executed, to train a unit by machine learning, by performing the training method for training a unit by machine learning of claim 16 when executed on the training system for training a unit by machine learning of claim 9.

* * * * *